(12) United States Patent
Sun et al.

(10) Patent No.: US 10,124,331 B2
(45) Date of Patent: Nov. 13, 2018

(54) OPTOFLUIDIC LASERS WITH SURFACE GAIN AND METHODS OF MAKING AND USING THE SAME

(71) Applicant: BOARD OF REGENTS, THE UNIVERSITY OF TEXAS SYSTEM, Austin, TX (US)

(72) Inventors: Yuze Sun, Grand Prairie, TX (US); Han Zhang, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/649,703

(22) Filed: Jul. 14, 2017

(65) Prior Publication Data

US 2018/0015456 A1 Jan. 18, 2018

Related U.S. Application Data

(60) Provisional application No. 62/362,658, filed on Jul. 15, 2016.

(51) Int. Cl.

| | |
|---|---|
| *G01N 21/55* | (2014.01) |
| *B01L 3/00* | (2006.01) |
| *G02B 6/12* | (2006.01) |
| *G01N 21/64* | (2006.01) |
| *C12M 1/34* | (2006.01) |
| *G02B 6/122* | (2006.01) |
| *B82Y 20/00* | (2011.01) |

(52) U.S. Cl.
CPC ............. *B01L 3/5027* (2013.01); *B82Y 20/00* (2013.01); *C12M 1/3476* (2013.01); *G01N 21/6458* (2013.01); *G02B 6/12007* (2013.01); *G02B 6/1225* (2013.01); *B01L 3/502715* (2013.01)

(58) Field of Classification Search
CPC . B01L 3/5027; G02B 6/1225; G02B 6/12007; G01N 21/6458; G01N 33/146; G01N 21/65; G01N 21/05
USPC .................................. 356/244, 246, 301, 445
See application file for complete search history.

(56) References Cited

U.S. PATENT DOCUMENTS

| | | | | |
|---|---|---|---|---|
| 7,525,722 | B2* | 4/2009 | Kolodner | G02B 26/004 359/296 |
| 8,068,229 | B2* | 11/2011 | Kolodner | G02B 26/004 356/445 |
| 9,151,713 | B2* | 10/2015 | Fan | G01N 21/6428 |
| 2008/0003142 | A1* | 1/2008 | Link | B01F 3/0807 422/82.08 |
| 2008/0159351 | A1* | 7/2008 | Li | H01S 3/022 372/53 |
| 2008/0245430 | A1* | 10/2008 | Adleman | B01L 3/50273 137/827 |

(Continued)

*Primary Examiner* — Hoa Pham
(74) *Attorney, Agent, or Firm* — John P. Zimmer; Nexsen Pruet, PLLC

(57) ABSTRACT

In one aspect, optofluidic lasers are described herein. In some embodiments, an optofluidic laser described herein comprises a first liquid having a first refractive index, a second liquid having a second refractive index that is different than the first refractive index, and a liquid-liquid interface defined by the first and second liquids and disposed between the first and second liquids. Moreover, the first and second liquids are immiscible. Additionally, the optofluidic laser further comprises a layer of gain material disposed at the liquid-liquid interface between the first and second liquids.

20 Claims, 7 Drawing Sheets

(56) References Cited

U.S. PATENT DOCUMENTS

2010/0277721 A1* 11/2010 Kolodner ............. G02B 26/004
 356/213
2013/0222799 A1* 8/2013 Ashok ............... B01L 3/502715
 356/301
2013/0344532 A1* 12/2013 Dupoy ............... G01N 21/6486
 435/34

* cited by examiner

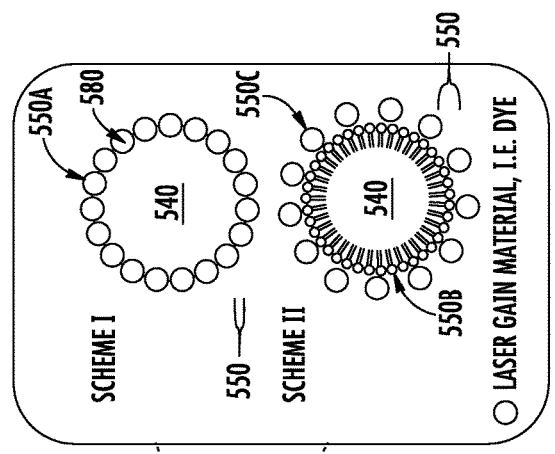
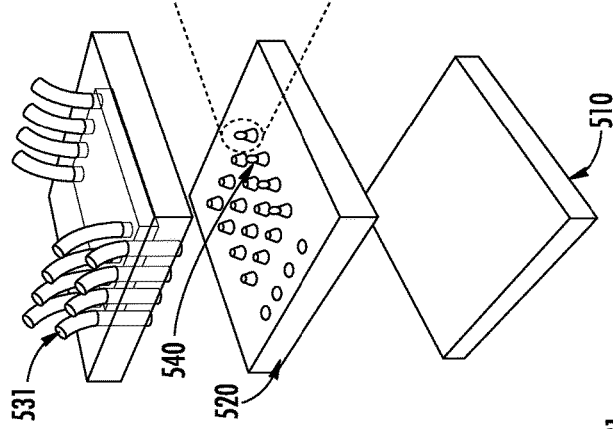
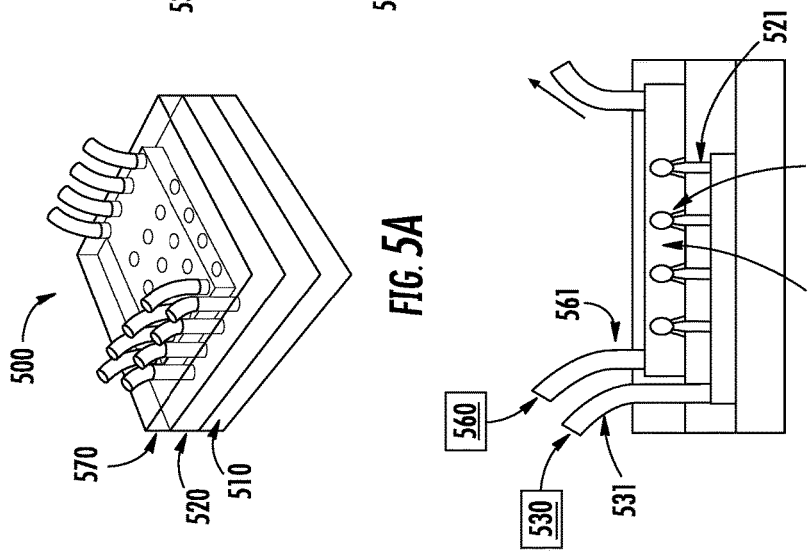
FIG. 5A
FIG. 5B
FIG. 5C
FIG. 5D

OPTOFLUIDIC LASERS WITH SURFACE GAIN AND METHODS OF MAKING AND USING THE SAME

CROSS REFERENCE TO RELATED APPLICATIONS

This application claims priority pursuant to 35 U.S.C. § 119(e) to U.S. Provisional Patent Application Ser. No. 62/362,658, filed on Jul. 15, 2016, which is hereby incorporated by reference in its entirety.

STATEMENT REGARDING FEDERALLY SPONSORED RESEARCH

This invention was made with government support under contract 1554013 awarded by the National Science Foundation. The government has certain rights in the invention.

FIELD

This application relates to optofluidic devices and, more particularly, to optofluidic lasers and methods of making and using optofluidic lasers.

BACKGROUND

Optofluidics is a field that synergizes photonics and micro/nanofluidics to achieve enhanced functionalities in both fluidics and photonic devices. The optofluidic laser is an emerging research area within optofluidics. In general, optofluidic lasers integrate micro/nanofluidics, optical microcavities, and gain material in a liquid environment. Compared to gas- and solid-state lasers, optofluidic lasers are compatible with liquid environments. Accordingly, optofluidic lasers can provide certain advantages for some applications, including some applications that involve aqueous environments, such as some biosensing applications.

In optofluidic laser biosensing, biological processes or events take place inside a laser cavity (rather than a container such as a test tube). Thus, rather than using unamplified fluorescence to detect biological processes or events, optofluidic laser biosensing uses lasing emission. More particularly, a biological process or event causes a change in the gain material associated with the laser cavity, and this change in turn causes a change in the laser output.

Unfortunately, previous optofluidic lasers and methods of optofluidic laser sensing suffer from one or more disadvantages. For example, many previous optofluidic lasers use a bulk solution that contains the gain material, which can be problematic in several regards. First, a large quantity of gain material is generally required to be present in the bulk solution, which lowers the detection sensitivity of the laser and deteriorates the laser performance. Second, in many previous optofluidic lasers, only gain material close to the cavity surface participates in the laser emission. The remaining gain material contributes to undesirable background fluorescence, decreasing the signal to noise ratio (SNR). Other optofluidic lasers are operable only in organic solvents and thus are not biocompatible. Still other previous optofluidic lasers use optical cavities having low Q-factors (e.g., $10^2$-$10^3$). Additionally, many previous optofluidic lasers cannot be readily reused or reconfigured, or easily mass-produced to form high-throughput laser arrays including a large number of individual lasing cavities.

Therefore, a need exists for improved optofluidic lasers and methods of making and using optofluidic lasers, including for high-throughput biosensing applications.

SUMMARY

Optofluidic lasers and methods of making and using the same are described herein. Such lasers and methods, in some cases, can provide one or more advantages compared to some previous lasers and methods. For example, in some instances, optofluidic lasers described herein are customizable regarding size, quantity, and/or gain materials used. Optofluidic lasers described herein, in some embodiments, also have a low lasing threshold and/or a high Q-factor. Moreover, in some cases, optofluidic lasers described herein are bioconfigurable (i.e., have lasing output that is responsive to the presence of bioanalytes) and/or biocompatible (i.e., can be used in biological and/or aqueous environments). Additionally, optofluidic lasers and methods described herein, in some embodiments, use small quantities (e.g., a single monolayer) of self-assembling gain material, thereby exhibiting reduced background fluorescence, improved sensitivity, and reduced cost compared to other lasers. Components of optofluidic lasers described herein can also be reusable and/or reconfigurable. Further, optofluidic lasers described herein can permit high-throughput screening of various analytes or test solutions, including for biological applications.

An optofluidic laser described herein, in some embodiments, comprises a first liquid having a first refractive index, a second liquid having a second refractive index that is different than the first refractive index, and a layer of gain material. Moreover, the first and second liquids are immiscible, such that a liquid-liquid interface defined by the first and second liquids forms or is disposed between the first and second liquids. Additionally, the layer of gain material is disposed at and/or confined to the liquid-liquid interface between the first and second liquids.

Further, in some embodiments of an optofluidic laser described herein, the second liquid forms one or more microdroplets within the first liquid, such that the liquid-liquid interface between the first and second liquids is defined by the exterior surface of the one or more microdroplets. Such microdroplets can define optical or lasing microcavities, including microcavities capable of supporting whispering gallery modes (WGMs). Moreover, in some cases in which a plurality of microdroplets is formed, the microdroplets form or define a two-dimensional array of microdroplets within the first liquid.

As described above, an optofluidic laser described herein, in some instances, includes only a small amount of gain material. In some embodiments, for example, the layer of gain material used in the optofluidic laser is a monolayer of gain material. Additionally, the layer of gain material may be formed from one or more amphiphilic molecules. In some cases, the amphiphilic molecules are luminescent. For example, the amphiphilic molecules may be fluorescent. In other instances, the layer of gain material is formed from amphiphilic molecules that are coupled to one or more fluorophores or luminescent/fluorescent species. In some such embodiments, the amphiphilic molecules are not luminescent themselves.

In addition, in some cases, an optofluidic laser described herein further comprises one or more recognition molecules at the liquid-liquid interface of the laser. In some embodiments, the recognition molecules are coupled to the layer of gain material. As described further hereinbelow, such recognition molecules can interact with analytes in the first or second liquid for detecting or sensing applications.

An optofluidic laser described herein, in some cases, also comprises a substrate over which the first liquid and the second liquid are disposed, and/or a light source for exciting the layer of gain material.

In another aspect, methods of making an optofluidic laser are described herein. In some embodiments, such a method comprises providing a first liquid phase and introducing a second liquid phase into the first liquid phase. The second liquid phase is immiscible with the first liquid phase. For example, in some cases, the first liquid phase is hydrophilic and the second liquid phase is hydrophobic. Moreover, the first liquid phase and the second liquid phase can have different refractive indices. Further, in some instances, the second liquid phase forms one or more microdroplets within the first liquid phase. Such microdroplets can form or define one or more optical or lasing microcavities of the optofluidic laser.

Additionally, the first liquid phase or the second liquid phase of a method described herein may include a gain material dispersed therein. The method may further include self-assembling a layer of the gain material at a liquid-liquid interface between the first liquid phase and the second liquid phase. The layer of gain material can comprise any of the species described hereinabove for the gain material of an optofluidic laser. Further, in some embodiments, the gain material forms a monolayer at the liquid-liquid interface.

In yet another aspect, methods of sensing using an optofluidic laser are described herein. In some cases, such a method comprises providing a first liquid phase and introducing a second liquid phase into the first liquid phase, wherein the second liquid phase is immiscible with the first liquid phase, and wherein the first liquid phase or the second liquid phase comprises a gain material dispersed in the first liquid phase or the second liquid phase, respectively. The method further comprises forming a layer of the gain material at a liquid-liquid interface between the first liquid phase and the second liquid phase; exposing the first and second liquids to electromagnetic radiation having a wavelength corresponding to an excitation wavelength of the gain material; detecting photoluminescence emitted by the gain material; and correlating the photoluminescence emitted by the gain material to a presence or absence and/or a concentration of an analyte within the first liquid phase and/or second liquid phase in an amount above a minimum detection threshold.

In addition, in some cases, one or more recognition molecules are present at the interface between the first liquid phase and the second liquid phase. Such recognition molecules can selectively interact with the analyte, and this interaction can alter one or more optical or lasing properties of the optofluidic laser. In this manner, the presence or amount of an analyte can be sensed or detected. For example, in some instances, the presence of the analyte alters the lasing efficiency of the gain material compared to the absence of the analyte. For instance, in some embodiments, the presence of the analyte reduces the intensity of the photoluminescence of the gain material compared to the absence of the analyte. Alternatively, in other cases, the presence of the analyte increases the intensity of the photoluminescence of the gain material compared to the absence of the analyte. It is also possible for the presence of the analyte to alter the peak emission wavelength and/or the peak excitation wavelength of the gain material compared to the absence of the analyte. In still other embodiments, the presence of the analyte alters the photoluminescence quantum yield of the gain material compared to the absence of the analyte. In some cases, the presence of an analyte alters the polarization and/or lasing mode spatial profile of the gain material emission, compared to the absence of the analyte. The analyte of a method of sensing described herein may include one or more of a biomolecule, tissue, cell, DNA, or RNA.

These and other embodiments are described in more detail in the detailed description which follows.

BRIEF DESCRIPTION OF THE FIGURES

FIG. 5A schematically illustrates a perspective view of an optofluidic laser used for sensing according to one embodiment described herein.

FIG. 5B schematically illustrates a sectional view of an optofluidic laser used for sensing according to one embodiment described herein.

FIG. 5C schematically illustrates an exploded view of an optofluidic laser used for sensing according to one embodiment described herein.

FIG. 5D schematically illustrates layers of gain material for optofluidic lasers according to some embodiments described herein.

DETAILED DESCRIPTION

Figure 1A:
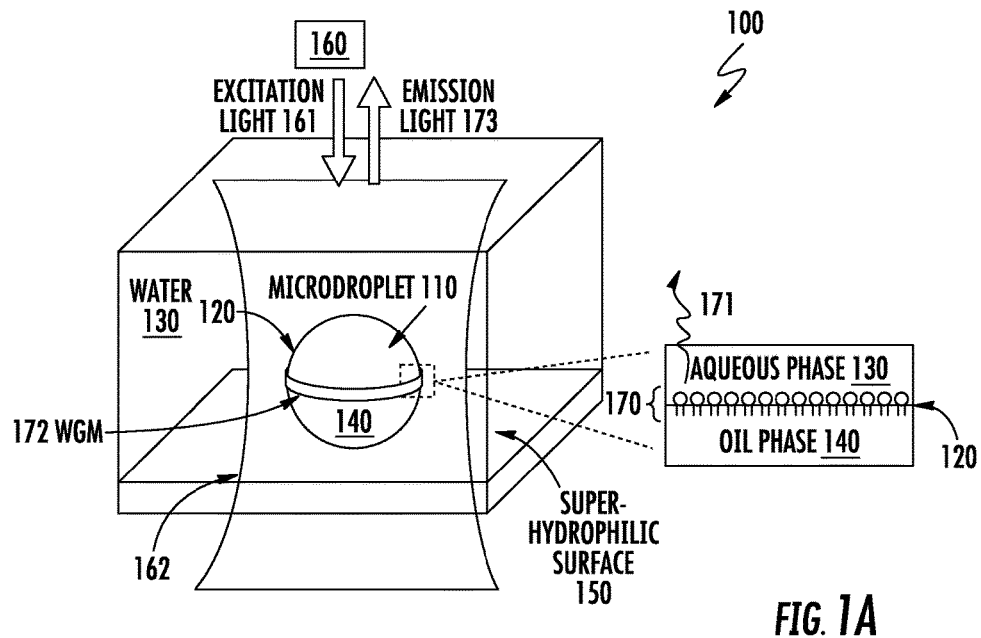
FIG. 1A schematically illustrates an optofluidic laser according to one embodiment described herein.

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" or "from 5 to 10" or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

I. Optofluidic Lasers

In one aspect, optofluidic lasers are described herein. In some embodiments, optofluidic lasers described herein utilize droplet type microcavities formed in an all liquid environment. The microcavities are formed at a liquid-liquid interface between at least two immiscible liquids. A small quantity of gain material self-assembles at the liquid-liquid interface. Not intending to be bound by theory, it is believed that this "surface-gain" geometry at the interface permits the control, modification, programming, and engineering of the laser gain at the molecular level through interaction of the gain material with various other species present in the liquid system, such as species having biological functionalities or bio-active moieties (e.g., DNA, protein, cells, lipids, adenosine triphosphate (ATP), or ions).

Turning now to specific components of optofluidic lasers, optofluidic lasers described herein comprise a first liquid or liquid phase and a second liquid or liquid phase. Any combination of first and second liquids or liquid phases not inconsistent with the objectives of the present disclosure may be used in an optofluidic laser described herein. For example, in some embodiments, the first liquid or liquid phase is aqueous or hydrophilic, and the second liquid or liquid phase is hydrophobic. Moreover, in general, the first and second liquids or liquid phases are immiscible, including at a temperature of 20-30° C. Two liquids or liquid phases that are "immiscible," for reference purposes herein, cannot be mixed or blended to form a single homogeneous liquid phase. As understood by one of ordinary skill in the art, two immiscible liquids may mix to some degree (e.g., by means of one liquid partially or slightly dissolving the other liquid) without thereby becoming "miscible." Further, in some embodiments, a first (or second) liquid described herein dissolves no greater than 10 mol. %, no greater than 5 mol. %, no greater than 3 mol. %, no greater than 1 mol. %, or no greater than 0.5 mol. % of a second (or first) liquid described herein.

Such immiscible liquids or liquid phases can form or define a liquid-liquid interface when the two liquids are combined. It is further to be understood that the liquid-liquid "interface" can be a single continuous interface (such as might be formed by a first liquid layer disposed on top of a second liquid layer) or a discontinuous interface (such as might be formed by a second liquid being dispersed as droplets within a continuous first liquid). Additionally, a liquid-liquid interface described herein can be planar or non-planar or curved. In some cases, the liquid-liquid interface is a surface area of a sphere, a hemisphere, or any portion thereof. Such a curved, spherical, or hemispherical liquid-liquid interface can be especially advantageous for forming or defining a microcavity that supports WGMs through total internal reflection of light emitted by a gain material at or near the interface.

In some embodiments, one of the first and second liquids or liquid phase materials forms a plurality of microdroplets in the other of the first and second liquids or liquid phase materials. Further, in some such instances, the plurality of microdroplets may be arranged in a two-dimensional array of microdroplets, thereby providing an array of optical microcavities or an array of optofluidic lasers. Any array not inconsistent with the objectives of the present disclosure may be used. For example, in some cases, the array is an ordered array of linear "rows and columns" of microdroplets (or microcavities or lasers), as defined in two or three dimensions (e.g., on an xy-plane parallel to a substrate surface described herein). In other instances, the array is a regularly patterned or symmetric array in two or three dimensions but does not necessarily include ordered rows and columns of microdroplets (or microcavities or lasers). In still other embodiments, a plurality of microdroplets (or microcavities or lasers) forms a non-ordered or random "array" of microdroplets (or microcavities or lasers) in two or three dimensions.

In addition, the microdroplets can have any size not inconsistent with the objectives of the present disclosure. In some cases, the microdroplets have a size sufficient to support a WGM of luminescent emission of the gain material of the optofluidic laser (where, as understood by one of ordinary skill in the art, the particular size needed to support a WGM can vary based on the luminescent emission wavelength of the gain material). For instance, where a plurality of microdroplets forms, the microdroplets can range in diameter from approximately 10 to 500 micrometers (μm) or approximately 30 to 500 μm. The microdroplets may also be smaller than 10 μm or 30 μm, or larger than 500 μm. In some embodiments, the plurality of microdroplets have an average diameter of approximately 10 μm or more, 30 μm or more, 50 μm or more, 80 μm or more, 100 μm or more, 150 μm or more, 200 μm or more, or 300 μm or more. In some cases, the microdroplets have an average diameter of 10-500 μm, 20-500 μm, 30-500 μm, 10-400 μm, 30-400 μm, 10-300 μm, 30-300 μm, 50-500 μm, 50-400 μm, 50-300 μm, 50-200 μm, 100-500 μm, 100-400 μm, 100-300 μm, or 100-200 μm. Additionally, the size, shape, and/or number of microdroplets formed in a manner described herein, in some embodiments, can be selected based on one or more of the chemical identities of the first and second liquids, the relative amounts of the first and second liquids, and the number and/or arrangement of nozzles or other components used to dispense liquid phase materials as described hereinbelow.

Further, the first and second liquids or liquid phases of an optofluidic laser described herein can have differing optical properties. For example, in some embodiments, the two liquid phase materials have different refractive indices (n). Suitable liquid phase materials may include water or an aqueous solution (wherein n is approximately 1.334) and silicones or other oils (wherein n=1.336 to 1.582) such as mineral oil (wherein n is approximately 1.515). Moreover, the refractive indices of the first and second liquids can differ by at least 0.01, at least 0.05, at least 0.1, at least 0.15, at least 0.18, at least 0.20, at least 0.22, or at least 0.24. In some cases, the refractive indices of the first and second liquid differ by 0.01-0.4, 0.05-0.4, 0.05-0.3, 0.1-0.4, 0.1-0.3, 0.1-0.25, 0.1-0.2, 0.15-0.4, 0.15-0.3, 0.15-0.25, or 0.2-0.4. Additionally, in some embodiments wherein one liquid forms a plurality of droplets within another liquid, the liquid that forms the droplets (the "internal" or "interior" liquid) has the higher refractive index.

The phase segregation and optical properties of the first and second liquids can be used to form one or more optical microcavities or other optical resonators, which may also be referred to as laser cavities or resonators. Such cavities, microcavities, or resonators can provide feedback and amplification of light emission generated by the excitation of a gain material described herein. Further, in some embodiments, the microcavities exhibit a high quality factor (Q-factor) resulting from a lower rate of energy loss relative to the stored energy of the resonator. In some cases, the microcavities of optofluidic lasers described herein have Q-factors greater than $10^7$.

Moreover, in some embodiments, at least one of the liquids or liquid phases of an optofluidic laser described herein comprises one or more analytes and/or recognition molecules. Further, in some cases, the first liquid comprises one or more analytes, and the second liquid comprises one or more recognition molecules. More particularly, where used, the analytes may be provided in the liquid phase having the lower refractive index (e.g., an aqueous phase), and the recognition molecules may be provided in the liquid phase having the higher refractive index (e.g., a hydrophobic phase). However, the recognition molecules may also or alternatively be included in the opposite liquid phase if desired. Any analytes and recognition molecules not inconsistent with the objectives of the present disclosure may be used. For example, in some cases, the analytes include bio-analytes (e.g., analytes of biological interest or analytes that are themselves biomolecules, such as nucleic acids or proteins). Further, in some such instances, the recognition molecules include bio-recognition molecules (e.g., molecules that selectively bind to bio-analytes). More generally, the analytes and recognition molecules can comprise any pair or set of species that selectively interact with one another, such as through antibody binding, biotin-streptavidin binding, complementary single-strand deoxyribonucleic acid (DNA) or ribonucleic acid (RNA) binding, or other specific binding. Thus, a recognition molecule can be selected based on an analyte of interest, where the presence or absence of the analyte is to be determined or tested for in a manner described further hereinbelow. In some such cases, the recognition molecule selectively bonds to the analyte. In addition, as described further herein, the interaction between the analytes and recognition molecules may be detected by virtue of a change in the output of an optofluidic laser described herein (e.g., a change in emission maximum, lasing threshold, intensity, or quantum yield). Further, where used, the recognition molecules may be dispersed (uniformly or non-uniformly) within one or both of the two immiscible liquids (e.g., within microdroplets described herein). The recognition molecules may also be confined to or self-assembled at the liquid-liquid interface between the two immiscible liquids.

It is further to be understood that first and second liquids or liquid phase materials described herein can have any combination of properties and/or features described hereinabove not inconsistent with the objectives of the present disclosure.

Optofluidic lasers described herein also comprise a layer of gain material disposed at a liquid-liquid interface. As understood by one of ordinary skill in the art, a layer of gain material can emit light in response to being excited, such as through exposure to electromagnetic radiation from an excitation light source. Any gain material not inconstant with the objectives of the present disclosure may be used. However, in general, the gain material comprises one or more luminescent chemical species or fluorophores. For example, in some instances, the gain material comprises an organic dye such as a laser dye. In some embodiments, the gain material is formed from a plurality of amphiphilic molecules that are luminescent or non-luminescent. The attraction between the chemical groups or moieties forming an amphiphilic gain material and each of the respective immiscible liquids can facilitate self-assembly of the gain material, automatically, at the liquid-liquid interface. Moreover, where the gain material includes amphiphilic molecules that are non-luminescent, the amphiphilic molecules may be coupled to one or more fluorophores or luminescent species to provide a composite gain material species that is capable of self-assembling at a liquid-liquid interface described herein. Notably, the gain material can self-assemble at a microdroplet surface (i.e., a liquid-liquid interface defined by microdroplets of one liquid dispersed in another liquid). The layer of gain material can thus correspond to a surface geometry of a microdroplet, such as a surface of a sphere, hemisphere, or portions thereof. More generally, the layer of gain material may include a curved, rounded, or non-linear surface structure, area, or geometry.

Additionally, the layer of gain material can have any thickness and structure not inconsistent with the objectives of the present disclosure. For example, in some cases, the layer of gain material is a monolayer of gain material. A "monolayer" of gain material, for reference purposes herein, is formed from a single layer or "repeating unit" of gain material species. For example, in some instances, a monolayer of gain material comprises a single layer of amphiphilic fluorophores, wherein a polar end of the amphiphilic molecules contacts a first (hydrophilic) liquid described herein and a non-polar end of the amphiphilic molecules contacts a second (hydrophobic) liquid described herein. In other embodiments, a monolayer of gain material comprises a single "bi-layer" of amphiphilic molecules, such as may be formed by lipids. It is further to be understood that a "monolayer" of gain material described herein can be formed from a composite material comprising a non-luminescent amphiphilic molecule coupled to (e.g., through a covalent chemical bond) a fluorophore or luminescent species. The fluorophore or luminescent species can be any fluorophore or luminescent species not inconsistent with the objectives of the present disclosure. For example, the fluorophore or luminescent species can be a laser dye, quantum dot, luciferin, or fluorescent protein. The fluorophore of a gain material described herein can also comprise a Förster resonant energy transfer (FRET) donor-acceptor pair, such as provided by a fluorescent DNA tetrahedron nanostructure or other DNA scaffold. In some embodiments, a layer of gain material is formed from more than one monolayer. For instance, in some cases, the layer of gain material is 2-10 or 2-5 monolayers thick, where the "thickness" of a layer is understood to be along the dimension or direction extending directly from the first liquid phase to the second liquid phase. In some embodiments, a layer of gain material has an average thickness of 15 nm or less, 10 nm or less, or 5 nm or less. In some instances, a layer of gain material has an average thickness of 1-15 nm, 1-10 nm, 1-5 nm, 1-3 nm, 3-10 nm, 3-5 nm, 5-15 nm, or 5-10 nm.

A gain material described herein may also be bonded or coupled to a recognition molecule or species described herein. Further, such a gain material may also be present in a layer having a structure described hereinabove. In some embodiments, for example, one or more recognition molecules may be confined at the liquid-liquid interface via coupling to one or more molecules of gain material as described further herein. For example, a monolayer of gain material may self-assemble at the liquid-liquid interface, and recognition molecules may couple to the monolayer of gain materiel via covalent bonding, ionic bonding, or the like, thereby forming a bi-layer. The interaction between the analytes and recognition molecules may be used for biochemical sensing applications, including detecting the presence or absence of organic material, biomolecules, cells, tissue, protein, DNA, or the like.

Additionally, in some embodiments, an optofluidic laser described herein comprises gain material only or substantially only within the layer of gain material at the liquid-liquid interface, as opposed to also containing gain material elsewhere, such as within the bulk solution of the first liquid and/or the second liquid. In some cases, at least 80%, at least 85%, at least 90%, at least 95%, at least 98%, or at least 99% of the gain material is present in the layer of gain material at the liquid-liquid interface, the percentage being a weight percent or a mole percent. Thus, all or substantially all of the gain material or luminescent material of an optofluidic laser described herein can participate in lasing. In some instances, at least 80%, at least 85%, at least 90%, at least 95%, at least 98%, or at least 99% of the total gain material or luminescent material present in the components of an optofluidic laser described herein are able to participate in lasing, such as through a WGM of an optical microcavity described herein.

Gain materials for optofluidic lasers described herein can have any combination of properties and/or features described herein not inconsistent with the objectives of the present disclosure.

Optofluidic lasers described herein, in some embodiments, also comprise a substrate. In some embodiments, the liquids and gain material of the optofluidic laser are disposed on or between one or more substrates. Any substrate not inconsistent with the objectives of the present disclosure may be used. For example, in some instances, a substrate is a hydrophilic substrate or superhydrophilic substrate. In some cases, a substrate is formed from silicon or glass. In some embodiments, a substrate is formed from an organic polymer such as a polycarbonate (PC). Other materials may also be used. Further, in some instances, a substrate described herein forms or exhibits a high contact angle with a microdroplet described herein. In some cases, for example, the substrate (e.g., a superhydrophilic substrate) forms or exhibits a contact angle with a microdroplet (e.g., a hydrophobic microdroplet) of at least 90 degrees. In some embodiments, the contact angle is greater than 90 degrees, greater than 120 degrees, or greater than 150 degrees. In some instances, the contact angle is 100-180, 120-180, 120-160, or 140-180 degrees.

Optofluidic lasers described herein can also comprise a light source. In particular, an excitation light source may be used. Any such light source not inconsistent with the objectives of the present disclosure may be used. In some cases, the light source is a laser excitation source such as a diode laser. In other instances, the light source is a light emitting diode (LED) or a broadband excitation source. Moreover, an excitation light source described herein can provide any wavelength of light not inconsistent with the objectives of the present disclosure, such as ultraviolet (UV) light, visible light, near infrared (NIR) light, or infrared (IR) light.

An optofluidic laser described herein can have any combination of properties or features described herein not inconsistent with the objectives of the present disclosure. In some embodiments, for instance, an optical laser described herein has a combination of any two liquids or liquid phase materials recited herein, and any layer of gain material described herein.

II. Methods of Making an Optofluidic Laser

In another aspect, methods of making an optofluidic laser are described herein. In some embodiments, such a method comprises providing a first liquid phase and introducing a second liquid phase into the first liquid phase, wherein the second liquid phase is immiscible with the first liquid phase, and wherein the first liquid phase or the second liquid phase comprises a gain material dispersed in the first liquid phase or the second liquid phase, respectively. The method further comprises self-assembling a layer of the gain material at a liquid-liquid interface between the first liquid phase and the second liquid phase.

The first liquid phase, the second liquid phase, and the gain material can comprise any first liquid or liquid phase material, second liquid or liquid phase material, or gain material, respectively, described hereinabove in Section I. For instance, in some cases, the first liquid phase is hydrophilic and the second liquid phase is hydrophobic. Additionally, in some embodiments, the first liquid phase has a different refractive index than the second liquid phase. In such cases, the refractive indices of the first liquid phase and the second liquid phase can differ by any amount described hereinabove in Section I. For example, in some instances, the first liquid phase and the second liquid phase differ in refractive index by at least 0.15. Similarly, in some embodiments, the gain material forms a monolayer at the interface between the first and second liquid phases. As described above in Section I, the layer of gain material can be formed from luminescent amphiphilic species or from non-luminescent amphiphilic species coupled to one or more fluorophores.

Moreover, as described above in Section I, the first liquid phase and/or the second liquid phase can further comprise one or more analytes and/or one or more recognition species that selectively interact with the one or more analytes. For example, in some cases, the first liquid phase includes one or more analytes, and the layer of gain material includes or is coupled to one or more recognition molecules that selectively interact with the analytes.

Turning again to specific steps of methods of forming an optofluidic laser described herein, the first liquid phase and the second liquid phase can be provided and combined or mixed in any manner not inconsistent with the objectives of the present disclosure. For example, in some embodiments, providing the first liquid phase comprises dispensing the first liquid phase from a first set of microchannels, and introducing the second liquid phase comprises dispensing the second liquid phase from a second set of microchannels. Further, as described hereinabove in Section I, introducing the second liquid phase can also comprise forming one or more microdroplets of the second liquid phase within the first liquid phase. The one or more microdroplets can define one or more optical or lasing microcavities. Moreover, when a plurality of microdroplets of the second liquid phase is formed within the first liquid phase, the plurality of microdroplets can define an array of optical microcavities and thus an array of optofluidic lasers.

In some exemplary embodiments, a plurality of microcavities forms as microfluidic channels and/or nozzles dispense a hydrophobic second liquid phase into an aqueous first liquid phase, causing the hydrophobic liquid phase to form microdroplets within the aqueous liquid phase. Additionally, in some such instances, gain material carried by the hydrophobic liquid phase self-assembles at the liquid-liquid interface between the hydrophobic and aqueous phases simultaneously as the microchannels dispense the hydrophobic liquid phase containing the gain material.

Further, in some embodiments, the optofluidic laser is provided on, over, or between one or more substrates, such as one or more substrates described hereinabove in Section I. The liquid phases of the optofluidic laser may also be combined within a chamber, such as a chamber defined by one or more substrates. As described further hereinbelow, the chamber may be "reusable," such that an optofluidic laser or array of optofluidic lasers described herein can be "regenerated" or "reformed" within the chamber by rinsing or otherwise removing, and then replenishing or replacing the first and/or second liquid phases that define the optofluidic laser or optofluidic laser array.

For example, in some cases, the second liquid phase is introduced into the first liquid phase in a chamber, and the method further comprises removing the first liquid phase and/or the second liquid phase from the chamber and subsequently replacing the first liquid phase in the chamber with a new first liquid phase and/or replacing the second liquid phase in the chamber with a new second liquid phase, and self-assembling a new layer of gain material at a new liquid-liquid interface between the new first liquid phase and the second liquid phase, between the first liquid phase and the new second liquid phase, or between the new first liquid phase and the new second liquid phase within the chamber. In some cases, only one of the first liquid phase and the second liquid phase is removed (e.g., by rinsing) and replaced with a corresponding new liquid phase. For example, in some instances, only the first liquid phase is removed and replaced by a new first liquid phase. In such cases, the second liquid phase remains the same during the removal (e.g., rinsing) process. Alternatively, in other embodiments, both of the first and second liquid phases are removed (e.g., by rinsing) and replaced by corresponding new liquid phases. In such instances, the new first liquid phase and the new second liquid phase can effectively provide a new optofluidic laser and sensing platform.

Moreover, as described further herein, an optofluidic laser or optofluidic laser array formed in a manner described herein can be used to generate luminescence or laser emission that can be used for various applications, such as biosensing applications. Thus, in some cases, a method described herein further comprises exciting the gain material and emitting light from the gain material, such as by exposing the gain material to an excitation light source.

It is further to be understood that an optofluidic laser or optofluidic laser formed by a method described herein can have any combination of properties or features described herein not inconsistent with the objectives of the present disclosure.

III. Methods of Sensing Using an Optofluidic Laser

In yet another aspect, methods of sensing using an optofluidic laser are described herein. In some embodiments, such a method comprises providing a first liquid phase and introducing a second liquid phase into the first liquid phase, wherein the second liquid phase is immiscible with the first liquid phase, and wherein the first liquid phase or the second liquid phase comprises a gain material dispersed in the first liquid phase or the second liquid phase, respectively. The method further comprises forming a layer of the gain material at a liquid-liquid interface between the first liquid phase and the second liquid phase; exposing the first and second liquids to electromagnetic radiation having a wavelength corresponding to an excitation wavelength of the gain material; detecting photoluminescence emitted by the gain material; and correlating the photoluminescence emitted by the gain material to a presence or absence and/or a concentration of an analyte within the first liquid phase and/or second liquid phase in an amount above a minimum detection threshold.

In addition, in some cases, one or more recognition molecules or species are present at the interface between the first liquid phase and the second liquid phase. Such recognition molecules or species can selectively interact with the analyte, and this interaction can alter one or more optical or lasing properties of the optofluidic laser. In this manner, the presence or amount of an analyte can be sensed or detected. The one or more recognition molecules or species can comprise any recognition molecules or species described hereinabove in Section I.

Turning again to specific steps of methods of sensing described herein, it is to be understood that the first liquid phase, the second liquid phase, and the gain material can comprise any first liquid or liquid phase material, any second liquid or liquid phase material, and any gain material, respectively, described hereinabove in Section I. Similarly, the first and second liquid phases can be provided and combined or mixed in any manner described hereinabove in Section II.

Methods described herein also comprise exposing the first and second liquids to electromagnetic radiation having a wavelength corresponding to an excitation wavelength of the gain material. The first and second liquids can be exposed to such an excitation source in any manner not inconsistent with the objectives of the present disclosure, including in a manner described hereinabove in Section I.

In addition, methods of sensing described herein further comprise detecting photoluminescence emitted by the gain material. The emitted photoluminescence can be detected using any detector configuration not inconsistent with the objectives of the present disclosure. In some embodiments, for instance, a photoluminescence signal is detected using a detector comprising a camera or photon counter, such as a charge coupled device (CCD) or a photomultiplier tube (PMT). In some cases, the detector comprises a spectrometer. The detector may also comprise one or more optical fibers or other "light pipes" coupled to the camera, photon counter, or spectrometer. Other configurations may also be used.

Methods described herein also comprise correlating the photoluminescence emitted by the gain material to a presence, absence, or concentration of an analyte within a liquid phase. "Correlating," as used herein, does not necessarily refer to mathematical correlation, such as mathematical correlation of variables. Instead, "correlating" refers to using one or more properties or characteristics of the light emitted by the gain material to identify whether one or more analytes is present or absent within a liquid phase, or to identify a concentration of one or more analytes within the liquid phase. It is generally to be understood that a correlating step can include, without limitation, using a measured amount of light emitted by the gain material, using a measured photoluminescence quantum yield of the gain material, and/or using a measured fluorescence lifetime of a gain material (e.g., as compared against a baseline or "control" level) to determine whether an analyte is present or absent within a liquid phase, or to determine the concentration of an analyte within a liquid phase described herein.

More generally, the correlating step of a method of sensing described herein can be based on any metric, spectroscopic property, or other feature of the gain material and/or analyte not inconsistent with the objectives of the present disclosure. For example, in some instances, the presence (or increased concentration) of an analyte alters the amount of light emitted by the gain material, compared to the amount of light emitted by the gain material in the absence (or reduced concentration) of the analyte. In some cases, the presence (or increased concentration) of the analyte alters the photoluminescence quantum yield of the gain material. In some instances, the presence (or increased concentration) of an analyte reduces the quantum yield or amount of light emitted by the gain material, compared to when there is no analyte (or a reduced concentration of the analyte). Alternatively, in other embodiments, the presence (or increased concentration) of an analyte increases an amount of light emitted by the gain material and/or increases the quantum yield of the fluorophore, compared to when there is an absence (or reduced concentration) of the analyte. Additionally, in some cases, the presence (or increased concentration) of an analyte shifts the peak emission wavelength and/or the peak excitation or absorption wavelength of the gain material. Further, in some instances, the presence (or increased concentration) of an analyte alters the fluorescence lifetime of the gain material, compared to the absence (or reduced concentration) of the analyte. In still other embodiments, the presence (or increased concentration) of an analyte alters the polarization and/or lasing mode spatial profile of the gain material emission, compared to the absence (or reduced concentration) of the analyte.

Moreover, a method of sensing described herein can be used to detect the presence, absence, or concentration of a variety of possible analytes, including any analyte described hereinabove in Section I.

As described further herein, methods of sensing according to the present disclosure can use lasing emission as opposed to non-lasing emission. Therefore, small changes in interaction/process between an analyte and a recognition species or other component of the optofluidic laser can induce a small variation in the gain medium, which nevertheless results in a significant change in the laser output. In this manner, by monitoring the laser output, underlying interactions, such as biological interactions, can be detected, monitored, and analyzed with enhanced sensitivity. Additionally, in some embodiments, the underlying interaction may be analyzed over time, such that changes in the interaction can be detected or monitored.

It is further to be understood that a method of sensing described herein can have any combination of properties or features described herein not inconsistent with the objectives of the present disclosure.

Some embodiments described herein are further illustrated in the following non-limiting examples.

EXAMPLE 1

Optofluidic Laser

FIG. 1A schematically illustrates an exemplary embodiment of an optofluidic laser described herein. As illustrated in FIG. 1A, the optofluidic laser (100) includes one microdroplet (110) defined by a liquid-liquid interface (120) between an aqueous liquid phase (130) and a hydrophobic (oil) liquid phase (140). However, other similar microdroplets (not shown) may also be present. The microdroplets (110) of the oil phase (140) are generated by a microfluidic T-junction (not shown) and subsequently released into the aqueous phase (130). A super-hydrophilic surface or substrate (150) was used to support microdroplets (110) to allow them to be individually probed by a pump laser excitation light source (schematically labeled as 160 in FIG. 1A). Organic dye DiI(3), an amphiphilic molecule, was used as the gain material (170). The inset of FIG. 1A illustrates a single molecular layer of gain material (170) that is self-assembled at the liquid-liquid interface (120).

The light source (160) provides excitation light (161) in a focal zone (162) to the microdroplet (110) for exciting the gain material (170). In response to being impinged by the excitation light (161), the gain material (170) photoluminesces, and the photoluminescence (171) is coupled into a WGM (172) provided by the microdroplet (110). This light (171) then exits the microdroplet (110), providing a laser emission signal (173) that can be measured, detected, and/or correlated for various applications, as described further herein. For example, when analyte (not shown) is present in the aqueous phase (130), the optofluidic laser characteristics may be used for biosensing.

Figure 1B:
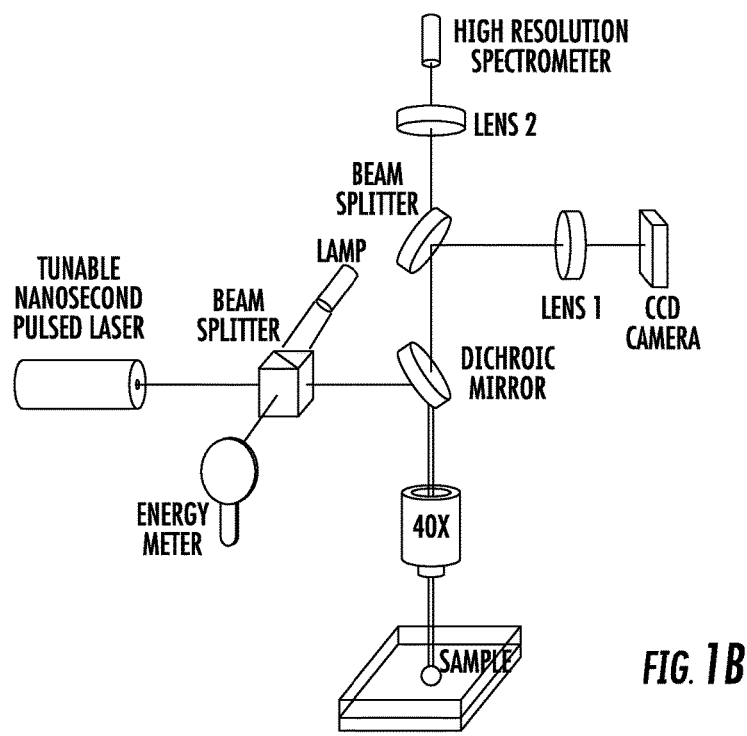
FIG. 1B schematically illustrates a method of using an optofluidic laser according to one embodiment described herein.

FIG. 1B illustrates an exemplary setup for lasing characterization. Microdroplet size is measured by a CCD camera. Lasing emission from the microdroplet is measured by a high resolution spectrometer.

Figure 2A:
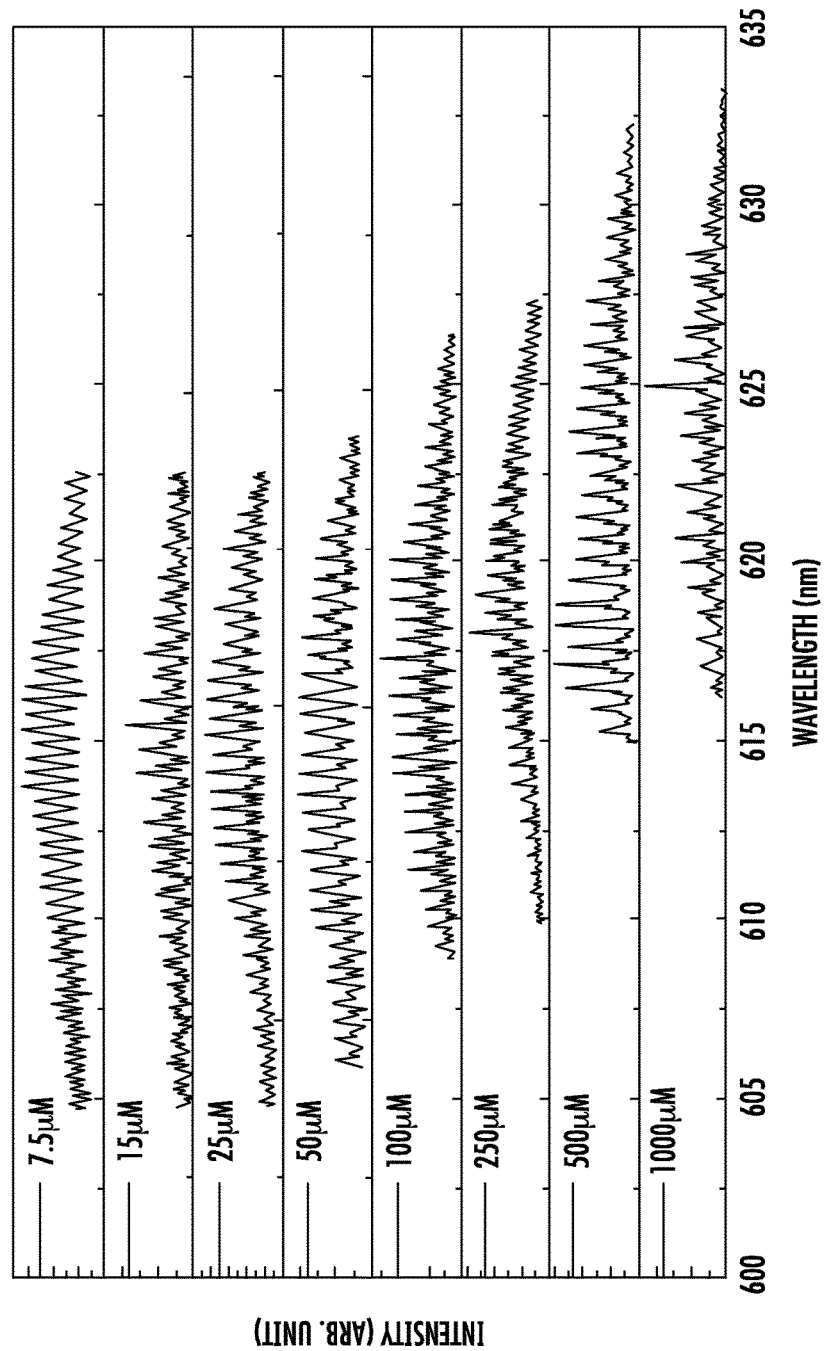
FIG. 2A illustrates lasing spectra associated with optofluidic lasers according to some embodiments described herein.
Figure 2B:
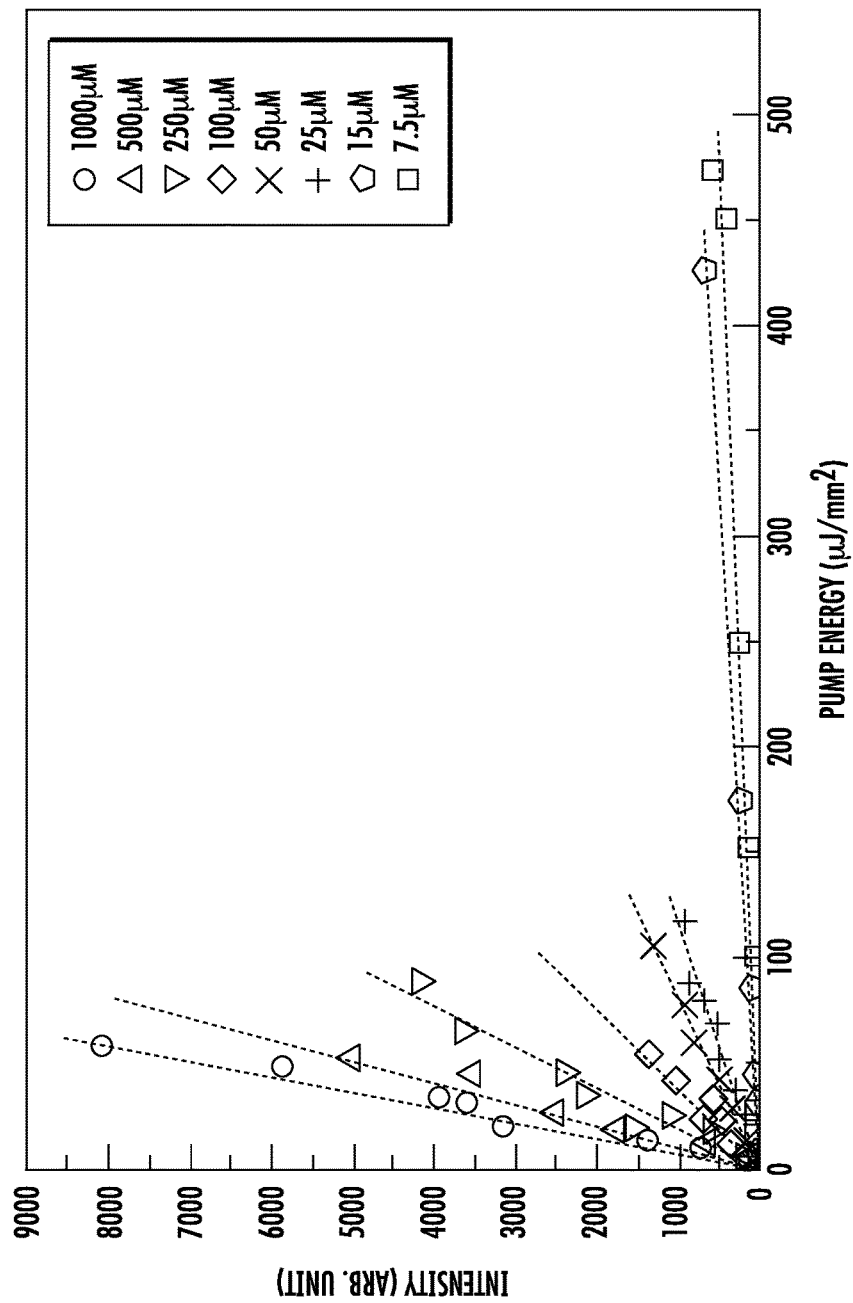
FIG. 2B illustrates lasing threshold curves for optofluidic lasers according to some embodiments described herein.

FIGS. 2A-3B illustrate exemplary results and/or characteristics associated with optofluidic lasers described herein. For example, FIG. 2A illustrates exemplary lasing spectra associated with microdroplets including different concentrations of gain material (DiI(3)). The gain material concentration varies from 7.5 µM to 1000 top to bottom. The smaller amounts of gain material provide a more sensitive laser. FIG. 2B illustrates exemplary lasing threshold curves for different concentrations of gain material (DiI(3)) in microdroplets.

Figure 3A:
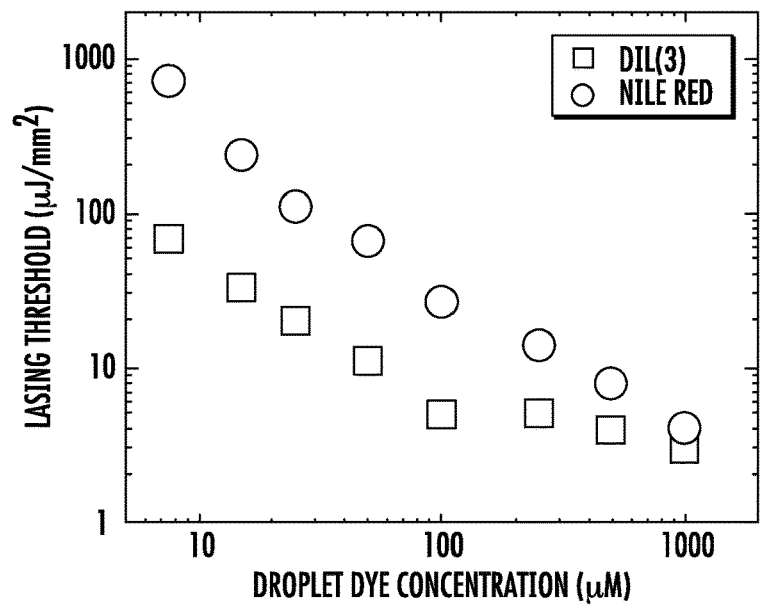
FIG. 3A illustrates lasing characteristics for an optofluidic laser according to one embodiment described herein.
Figure 3B:
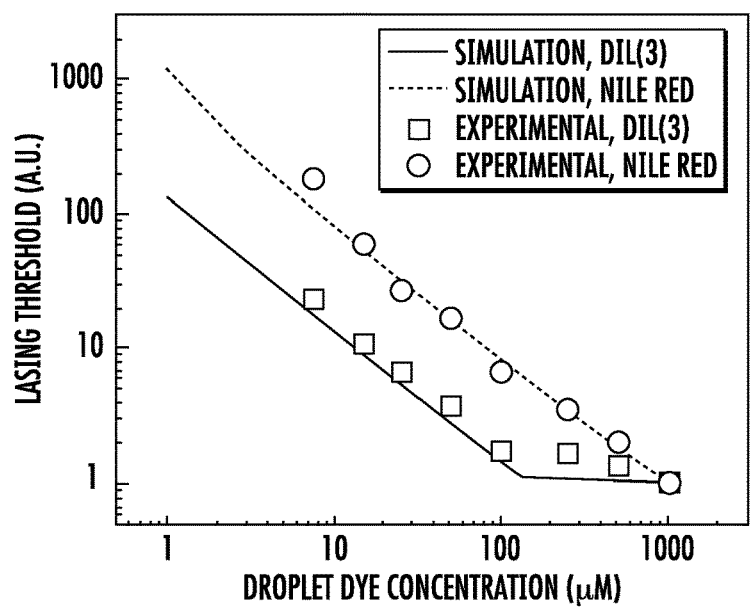
FIG. 3B illustrates lasing characteristics for an optofluidic laser according to one embodiment described herein.

FIG. 3A illustrates exemplary data that compares characteristics for two types of gain media. The line marked with circles (Nile Red) in FIG. 3A depicts characteristics of a non-surface geometry gain and the line marked with squares (DiI(3)) depicts characteristics of a surface-geometry gain associated with self-assembling gain material as described herein. FIG. 3A presents experimental data. FIG. 3B illustrates corresponding simulated data along with the experimental data. For the simulation, a microdroplet cavity Q-factor of $5 \times 10^3$ was used.

Figure 4:
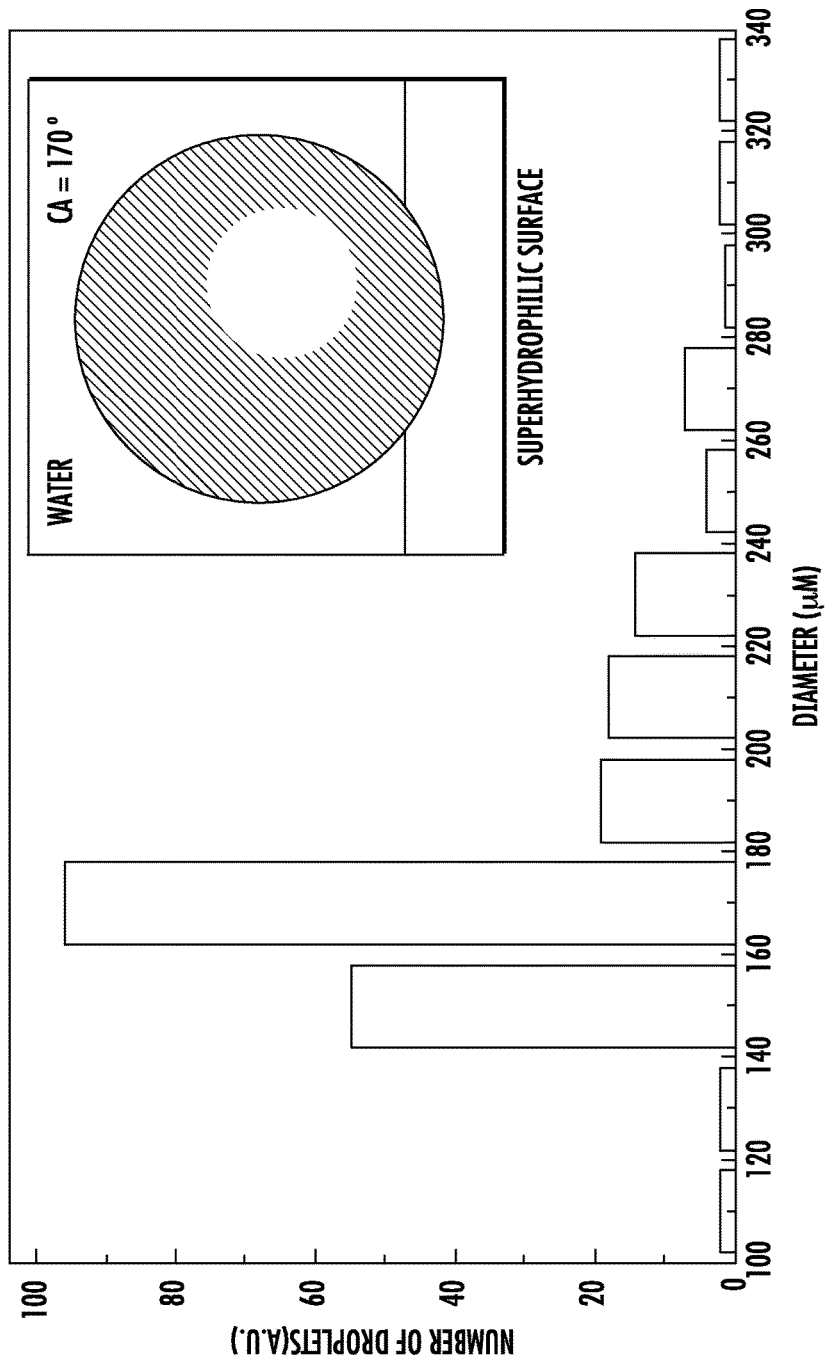
FIG. 4 illustrates a size distribution histogram of microdroplets used in optofluidic lasers according to some embodiments described herein.

FIG. 4 illustrates the size distribution of hydrophobic droplets generated at a microfluidic T-junction between a superhydrophilic surface and an aqueous liquid phase. As the inset of FIG. 4 illustrates, the hydrophobic liquid phase sits on and is supported by the superhydrophilic surface, and any number of droplets having any diameter may be provided in this manner. The contact angle of the hydrophobic droplet sitting on the hydrophilic surface measures approximately 170°.

Optofluidic lasers such as those described in this Example offer many advantages compared to other optofluidic lasers. For example, for optofluidic lasers having a monolayer of gain material at the liquid-liquid interface rather than including gain material in the droplet bulk solution allow all or substantially all of the gain material to participate in lasing. This substantially complete participation in lasing can result in greater than 1000-fold reduction in fluorescence background, and hence significantly improved sensitivity. Moreover, an optofluidic laser such as described herein, along with the integrated microfluidics, can provide the capability to introduce bio-analytes through the aqueous phase and allow them to access the microdroplet surface where the gain materials and bio-recognition molecules are located, as described in Example 2 below. The optofluidic laser structure depicted in FIGS. 1A-4 also provides ultra-high Q-factors ($>10^7$), which may be due to the atomically smooth surface and the low material absorption of the optical microcavity.

EXAMPLE 2

Optofluidic Laser Sensing

FIGS. 5A-6B illustrate various aspects of exemplary optofluidic lasers and their use for sensing applications, including but not limited to bio-sensing applications.

FIG. 5A is a schematic diagram of an optofluidic laser array sensing platform (500). The optofluidic laser array sensing platform (500) is provided over a substrate (510), such as a glass substrate. One or more microchannels (521) are disposed within a silicon wafer (520) that is provided over the glass substrate (510). The microchannels (521) are used to dispense a hydrophobic liquid phase (530) from one or more micronozzles or microchannels (531) extending through the Si wafer (520) to form a microdroplet (540). The hydrophobic phase (530) includes gain material including amphiphilic molecules (550A, 550B). The amphiphilic molecules may be luminescent themselves (550A in FIG. 5D), or non-luminescent (550B in FIG. 5D) and coupled to fluorescent molecules (550C in FIG. 5D). In some embodiments, the amphiphilic gain molecules (550A, 550B) are coupled to recognition molecules. In other embodiments, the recognition molecules are dispersed within or at the surface of the hydrophobic phase (530) forming the microdroplet (540).

An aqueous phase (560) is supplied from another set of microchannels and/or micronozzles (561) disposed above the hydrophobic phase (530). The aqueous phase (560) can include analytes, such as bio-analytes (e.g., biomolecules, cells, tissue, DNA, proteins, or the like) for interacting with recognition molecules, such as bio-recognition molecules.

FIG. 5B illustrates a sectional view of the optofluidic laser platform (500) of FIG. 5A. An array of microfluidic nozzles (521, 4×4 as illustrated in FIG. 5B, but this size can be readily scaled up or down) is fabricated on the Si wafer (520). As described above, the two sets of microfluidic nozzles or channels (531, 561) are designed to deliver the two immiscible fluids (530, 560) within a chamber or microfluidic channel (571) formed from or defined within a capping or cover layer (570), for example, a molded polydimethylsiloxane (PMDS) layer (570) defining an interior chamber or channel (571) that is placed over the silicon wafer (520). The first set of microfluidic channels (531, disposed over the glass (510)) are defined on the backside of the wafer (520) and are used for delivery of the hydrophobic phase (530) containing amphiphilic molecules to the micronozzles (521) and ultimately to the chamber or channel (571). The second set of microfluidic channels (561, disposed through the PDMS material or layer (570) forming the chamber (571)) are fabricated in PDMS and used for delivery of the aqueous (or hydrophilic) phase (560) containing bio-analytes.

When a positive pressure is applied to the bottom fluidic channels (531), an array of microdroplets (540, e.g., averaging in diameter from about 30-500 µm) is generated simultaneously on top of individual micro-nozzles (521) in the top fluidic channel (571). Concurrently, the amphiphilic molecules contained in the hydrophobic phase (560) self-assemble at the immiscible liquid-liquid interface (580) and form a monolayer of gain material (550). An accurate control on pressure can generate, fine-tune (size), release, and regenerate droplets (540) on-demand.

FIG. 5C is an exploded view of the three stacked layers forming an optofluidic laser sensing platform. In FIG. 5C, the microdroplets can be seen as sitting on or over the Si wafer substrate. The top microfluidic channels are used to deliver biological analytes in the aqueous (or hydrophilic) phase, whereas the bottom microfluidic channels are used to deliver the hydrophobic phase containing amphiphilic molecules (e.g., amphiphilic dyes, phospholipids labeled with fluorophores).

The microdroplets may include biorecognition material disposed therein that interacts with the bio-analytes. The biorecognition material may also be sequestered at the liquid-liquid interface via coupling with the gain material. The photoluminescence emitted by the gain material can be correlated to a presence or absence and/or a concentration of the bio-analyte in an amount above a minimum detection threshold, as described hereinabove. Moreover, after each measurement, the array can be easily regenerated by rinsing off the old droplets and forming new droplets.

FIG. 5D illustrates two exemplary types of surface-gain geometries. Scheme I schematically depicts a monolayer (550) of amphiphilic organic dye molecules (e.g., DiI(3), 550A) and Scheme II schematically depicts a phospholipid monolayer (550) formed from amphiphilic molecules (550B) labeled with luminescent gain molecules (550C). Both types of gain material can self-assemble at the droplet surface.

Structures similar to those described in FIGS. 5A-D above may also be formed using materials other than glass, silicon, and PDMS. It is also possible for a single material (rather than a plurality of differing materials, such as glass, silicon, and PDMS) to be used to form all of the device components described above. For example, in some cases, an optofluidic laser array can be formed or provided using polycarbonate (PC). In some such instances, an integrated optofluidic droplet laser system comprises a top microfluidic channel (analogous to 561, 571 and containing a water or aqueous phase) and a bottom microfluidic channel (analogous to 520, 531 and containing an oil or hydrophobic phase). The two channels can be bridged by a micro-nozzle structure (analogous to 521). The oil phase in the bottom channel is controlled by a high-precision syringe pump. Due to immiscibility between the phases, the oil phase forms a microdroplet (having a smooth surface) in the top microfluidic channel, as illustrated in FIG. 5. The size of the microdroplet can be accurately controlled by the syringe pump. Again, as described above, since the refractive index of the oil phase is higher than that of the water phase, whispering gallery modes (WGMs) are supported through total internal reflection (TIR) occurring at the microdroplet surface. Under external excitation, WGMs interact with the gain medium dissolved in the oil phase and provide feedback to the laser system. When the gain overcomes the total loss, lasing emission starts to emerge. Microdroplets can be released by water rinsing in the top microfluidic channel and further regenerated by pressurizing the bottom microfluidic channel. Advantages of using PC to form such a system include PC's low cost, good machining properties, high glass transition temperature (Tg of about 145° C.), high optical transparency at wavelengths in the visible range, and easy surface modification and biofunctionalization. Due to the good machining properties of PC, the fabrication of micro-nozzle structures can be carried out simply. Specifically, micro-nozzle structures and microfluidic channels can be created through micro-machining and then thermally bonded (125° C. for 45 min) to form a complete microfluidic device. Then the device can be treated by ethanolic solution of $SnCl_2$ [20% (w/w)] to make the PC surfaces hydrophilic, which can help to decrease the contact area between the microdroplet and the nozzle, and thus to achieve a higher Q-factor.

Figures 6A, 6B:
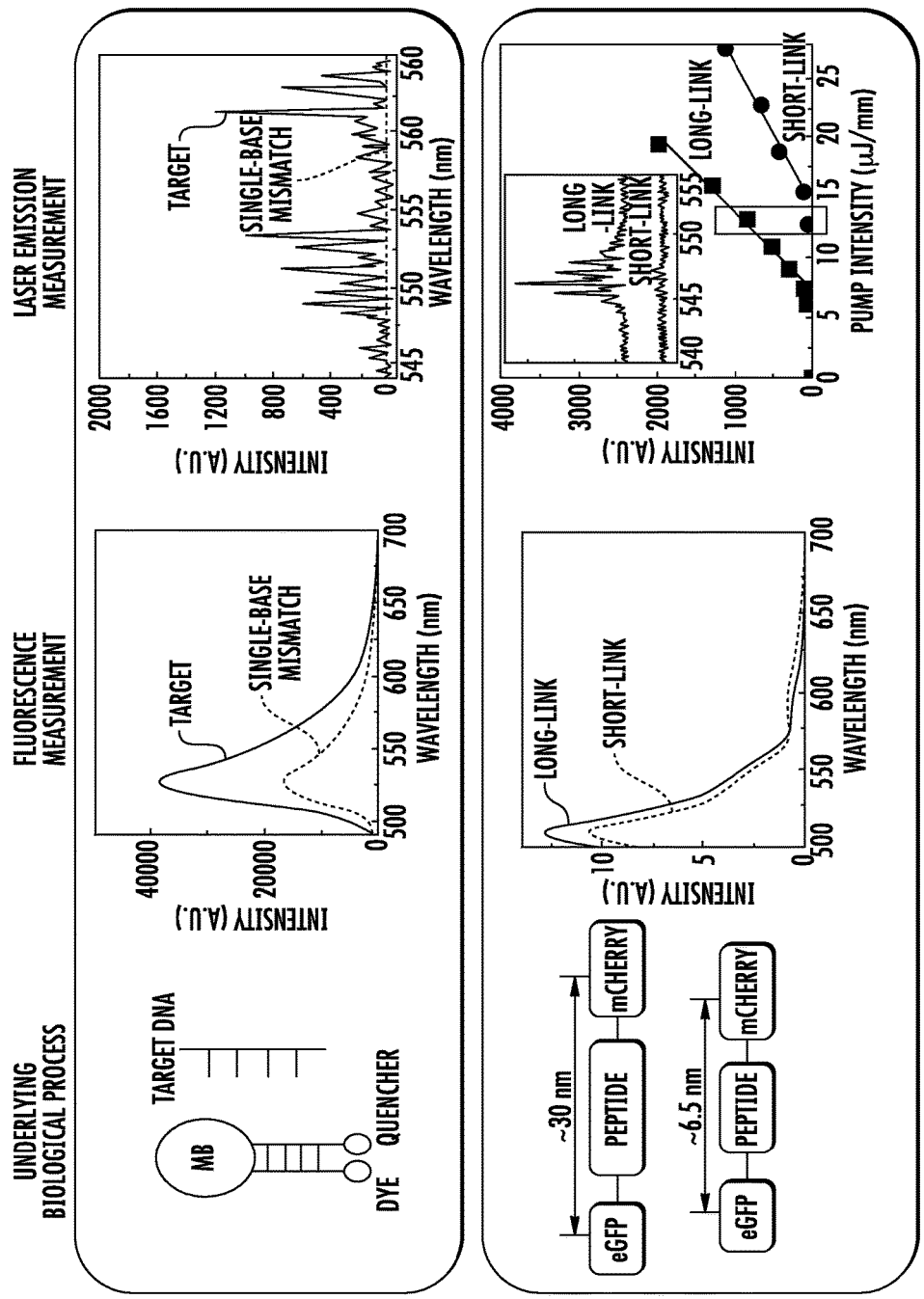
FIG. 6A schematically illustrates a method of sensing according to one embodiment described herein compared to a different method of sensing.
FIG. 6B schematically illustrates a method of sensing according to one embodiment described herein compared to a different method of sensing.

FIG. 6A provides a comparison between existing fluorescence-based detection (middle column, existing technology) and exemplary optofluidic laser based detection (right column) for the same biological interaction and process (left column). FIG. 6A illustrates detection of a single base mismatched DNA using a molecular beacon. Optofluidic laser based detection shows >200-fold improvement in the discrimination signal between the target and single-base-mismatched DNA.

FIG. 6B illustrates the sensitive detection of peptide length change using a fluorescent protein FRET pair. Optofluidic laser detection shows a 25× higher sensitivity than fluorescence based detection. There are also large differences in lasing threshold between long and short FRET pair. In contrast, there exists no such parameter (threshold) in fluorescence based detection.

Various embodiments of the present invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. An optofluidic laser comprising:
a first liquid having a first refractive index;
a second liquid having a second refractive index that is different than the first refractive index, wherein the first and second liquids are immiscible;
a liquid-liquid interface defined by the first and second liquids and disposed between the first and second liquids; and
a layer of gain material disposed at the liquid-liquid interface between the first and second liquids,
wherein the gain material is luminescent.

2. The laser of claim 1, wherein the second liquid forms at least one microdroplet within the first liquid.

3. The laser of claim 1, wherein the second liquid forms a plurality of microdroplets within the first liquid.

4. The laser of claim 3, wherein the plurality of microdroplets has an average diameter of 10 micrometers (μm) or more.

5. The laser of claim 3, wherein the plurality of microdroplets forms a plurality of optical microcavities and the plurality of optical microcavities support whispering gallery modes (WGMs) of light emitted by the layer of gain material.

6. The laser of claim 1, wherein the layer of gain material is a monolayer.

7. The laser of claim 1, wherein the layer of gain material is 2-5 monolayers thick.

8. The laser of claim 1, wherein the layer of gain material is formed from one or more amphiphilic molecules.

9. The laser of claim 8, wherein the amphiphilic molecules are luminescent.

10. The laser of claim 1, wherein the layer of gain material is formed from one or more non-luminescent amphiphilic molecules coupled to one or more luminescent species.

11. The laser of claim 1, wherein one or more recognition molecules are present at the liquid-liquid interface.

12. The laser of claim 11, wherein the recognition molecules are coupled to the layer of gain material.

13. The laser of claim 1, wherein the first liquid is an aqueous phase and the second liquid is a hydrophobic phase and wherein the hydrophobic phase forms a plurality of microdroplets in the aqueous phase.

14. The laser of claim 13, wherein the aqueous phase includes one or more analytes.

15. The laser of claim 14, wherein the hydrophobic phase includes recognition molecules that selectively interact with the one or more analytes.

16. The laser of claim 1, wherein the second refractive index is greater than the first refractive index.

17. The laser of claim 1, wherein a difference between the first refractive index and second refractive index is at least 0.01.

18. The laser of claim 1, further comprising:
a substrate over which the first liquid and the second liquid are disposed; and
a light source for exciting the layer of gain material.

19. A method of making an optofluidic laser, the method comprising:
providing a first liquid phase;
introducing a second liquid phase into the first liquid phase, wherein the second liquid phase is immiscible with the first liquid phase, and wherein the first liquid phase or the second liquid phase comprises a gain material dispersed in the first liquid phase or the second liquid phase, respectively; and
self-assembling a layer of the gain material at a liquid-liquid interface between the first liquid phase and the second liquid phase,
wherein the gain material is luminescent.

20. A method of sensing comprising:
providing a first liquid phase;
introducing a second liquid phase into the first liquid phase, wherein the second liquid phase is immiscible with the first liquid phase, and wherein the first liquid phase or the second liquid phase comprises a gain material dispersed in the first liquid phase or the second liquid phase, respectively;
forming a layer of the gain material at a liquid-liquid interface between the first liquid phase and the second liquid phase;
exposing the first and second liquids to electromagnetic radiation having a wavelength corresponding to an excitation wavelength of the gain material;
detecting photoluminescence emitted by the gain material; and
correlating the photoluminescence emitted by the gain material to a presence or absence and/or a concentration of an analyte within the first liquid phase and/or second liquid phase in an amount above a minimum detection threshold,
wherein the gain material is luminescent.

* * * * *